(12) United States Patent
Kortenhorst

(10) Patent No.: US 12,397,143 B2
(45) Date of Patent: Aug. 26, 2025

(54) DEVICE AND NEEDLE MODULE FOR PUNCTURING SKIN

(71) Applicant: MEDICAL PRECISION B.V., Zwolle (NL)

(72) Inventor: Roland Werner Francois Kortenhorst, Zwolle (NL)

(73) Assignee: MEDICAL PRECISION B.V., Zwolle (NL)

( * ) Notice: Subject to any disclaimer, the term of this patent is extended or adjusted under 35 U.S.C. 154(b) by 1021 days.

(21) Appl. No.: 16/769,636

(22) PCT Filed: Dec. 6, 2018

(86) PCT No.: PCT/NL2018/050815
§ 371 (c)(1),
(2) Date: Jul. 12, 2021

(87) PCT Pub. No.: WO2019/112430
PCT Pub. Date: Jun. 13, 2019

(65) Prior Publication Data
US 2021/0330953 A1    Oct. 28, 2021

(30) Foreign Application Priority Data

Dec. 6, 2017  (NL) .................................. 2020030
Apr. 4, 2018  (NL) .................................. 2020710
Apr. 24, 2018 (NL) .................................. 2020818

(51) Int. Cl.
*A61M 37/00* (2006.01)

(52) U.S. Cl.
CPC ................. *A61M 37/0084* (2013.01)

(58) Field of Classification Search
CPC .......... A61M 37/0076; A61M 37/0084; A61M 5/24; A61M 5/326; A61M 5/3287;
(Continued)

(56) References Cited

U.S. PATENT DOCUMENTS 2,800,882 A * 7/1957 Smith ................ B43K 24/08
                                                    401/112
2,863,421 A * 12/1958 Rizzo ................ B43K 24/08
                                                    401/113
(Continued)

FOREIGN PATENT DOCUMENTS

CN       2356645 Y    1/2000
CN     202236856 U    5/2012
(Continued)

OTHER PUBLICATIONS

International Search Report and Written Opinion, mailed May 2, 2019, for corresponding PCT/NL2018/050815.

*Primary Examiner* — Robert A Lynch
(74) *Attorney, Agent, or Firm* — KDW Firm PLLC

(57) ABSTRACT

A needle module for puncturing skin in a reciprocal manner. The needle module includes a needle unit, a housing and a biasing mechanism. The needle unit includes a needle. The needle unit is movable with respect to the housing between an extended position, in which a distal end of the needle extends from a distal end of the housing, and a retracted position, in which the distal end of the needle is positioned within the housing. The biasing mechanism is arranged for urging the needle unit towards the retracted position. The needle module further includes a limiting mechanism. The limiting mechanism is arranged for limiting the relative movement of the needle unit out of the distal end of the housing to a maximum extension distance when the needle unit is moving towards the extended position. The maximum extension distance is 1.5 mm or less.

20 Claims, 12 Drawing Sheets

(58) Field of Classification Search
CPC .......... A61M 5/3293; A61M 5/46; A61M 2005/206; A61M 2205/106; A61B 90/39; A61B 2090/034; A61B 2090/08021; A61B 2090/3933; A61B 2090/395; A61B 17/3494; A61B 17/3496

See application file for complete search history.

(56) References Cited

U.S. PATENT DOCUMENTS

| | | | | |
|---|---|---|---|---|
| 3,409,380 | A | * | 11/1968 | Longarzo ............. B43K 24/08 401/112 |
| 4,572,688 | A | * | 2/1986 | Klose ................. B43K 24/08 401/113 |
| 4,582,060 | A | | 4/1986 | Bailey |
| 4,665,912 | A | * | 5/1987 | Burton ............. A61M 37/0076 606/186 |
| 4,981,382 | A | * | 1/1991 | Murphy ............... B43K 24/08 401/109 |
| 5,496,304 | A | | 3/1996 | Chasan |
| 5,915,867 | A | * | 6/1999 | Hashimoto ........... B43K 8/028 401/108 |
| 2004/0024367 | A1 | | 2/2004 | Gilbert |
| 2006/0020283 | A1 | * | 1/2006 | Lisec ............... A61M 37/0076 606/185 |
| 2007/0223986 | A1 | * | 9/2007 | Rolion ................. B43K 7/12 401/109 |
| 2008/0287978 | A1 | * | 11/2008 | Hickman, III .... A61M 37/0076 606/186 |
| 2010/0191268 | A1 | * | 7/2010 | Lee ............... A61M 37/0084 606/185 |
| 2012/0271335 | A1 | * | 10/2012 | Lee ............... A61M 37/0084 606/185 |
| 2014/0018835 | A1 | | 1/2014 | Scherkowski et al. |
| 2014/0324089 | A1 | | 10/2014 | Chan et al. |
| 2014/0334864 | A1 | * | 11/2014 | Takahashi ............. B43K 7/02 401/99 |
| 2015/0025561 | A1 | * | 1/2015 | La Fontaine ..... A61M 37/0076 606/186 |
| 2016/0221382 | A1 | * | 8/2016 | Lee ................... B43K 24/08 |

FOREIGN PATENT DOCUMENTS

| | | |
|---|---|---|
| CN | 204502099 U | 7/2015 |
| DE | 202006013148 U1 | 8/2006 |
| EP | 2682146 A1 | 1/2014 |
| EP | 3246067 A1 | 5/2017 |
| KR | 101593639 B1 | 2/2016 |

* cited by examiner

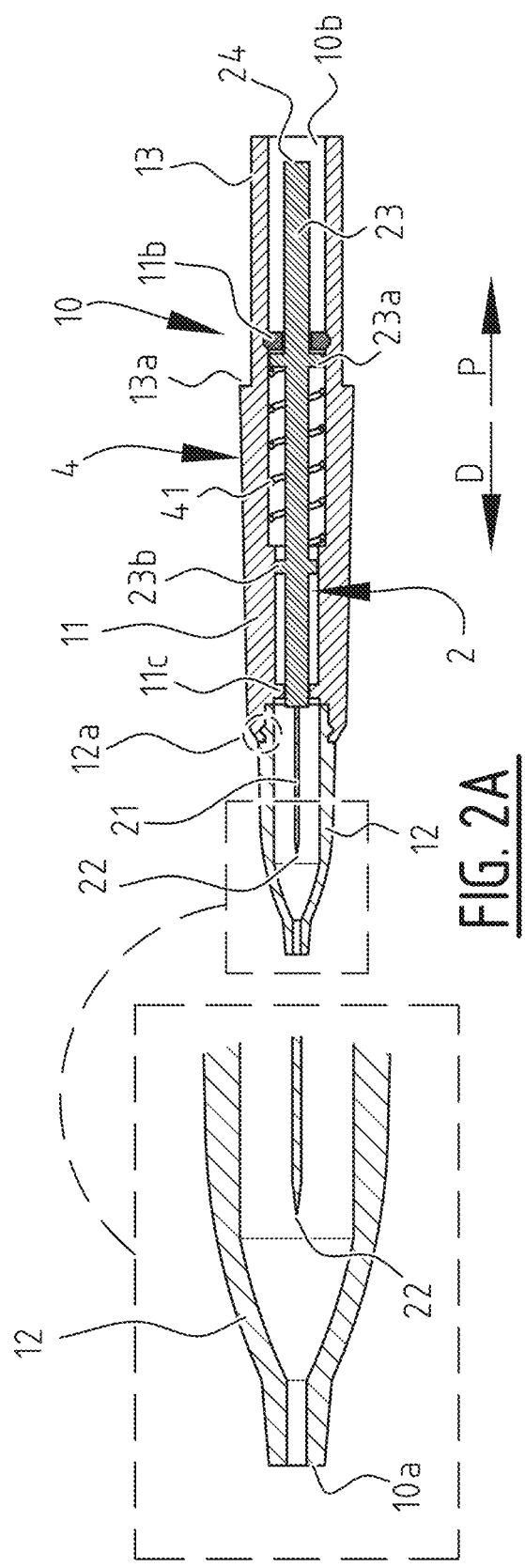
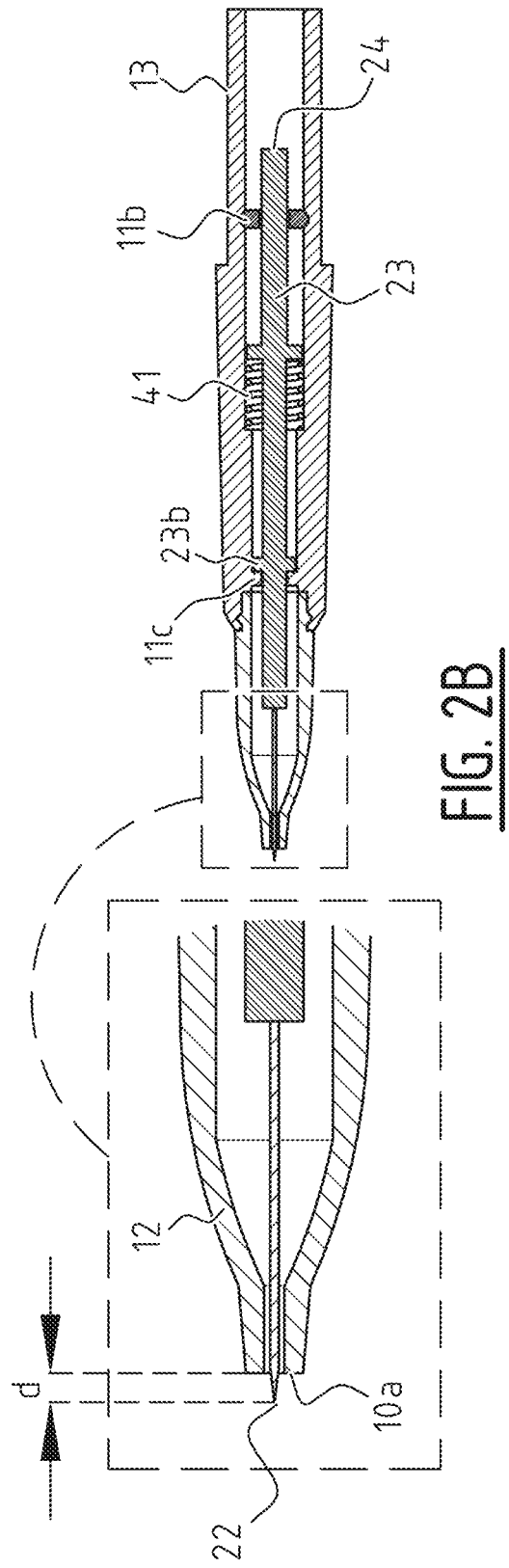
FIG. 2A
FIG. 2B

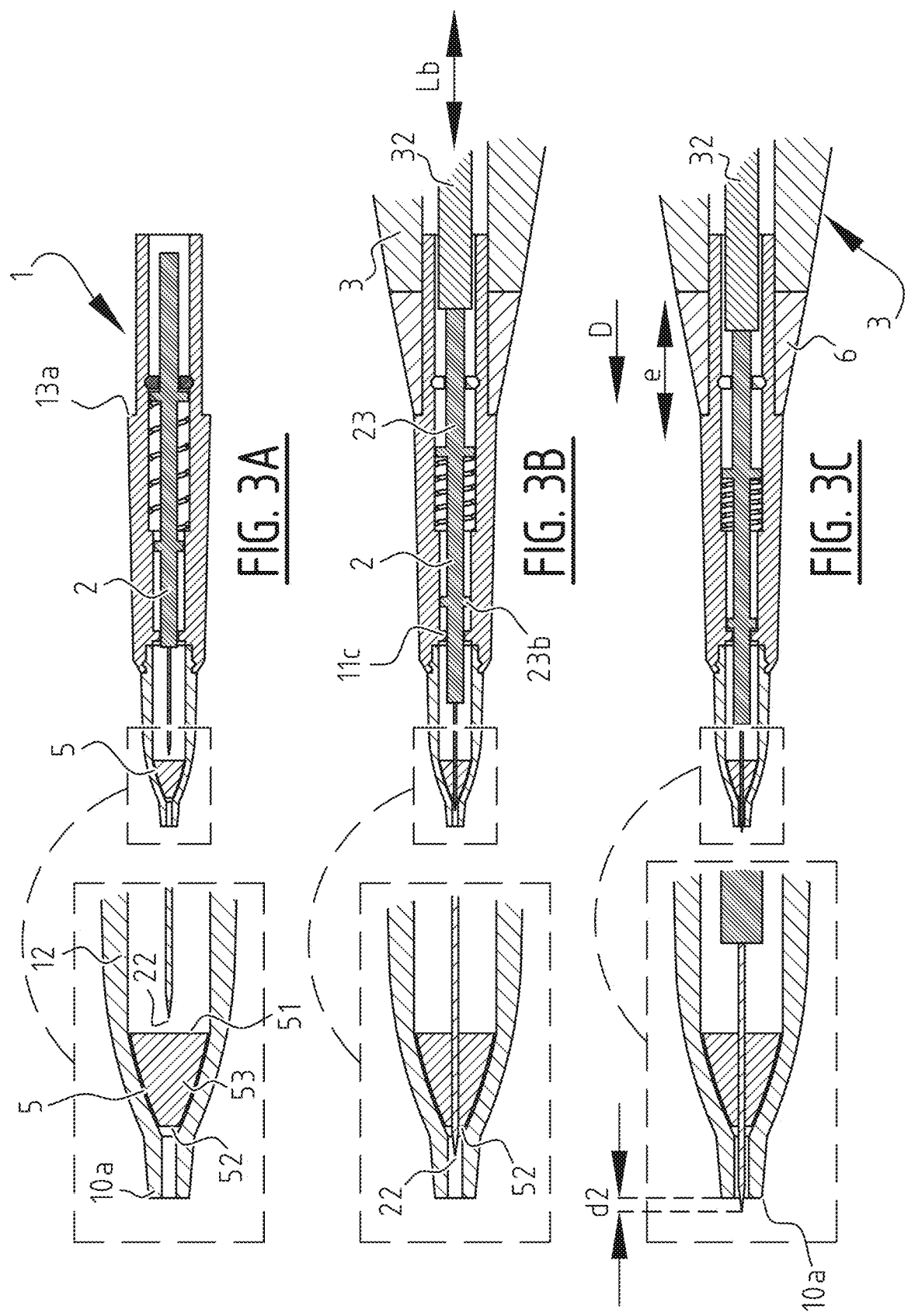

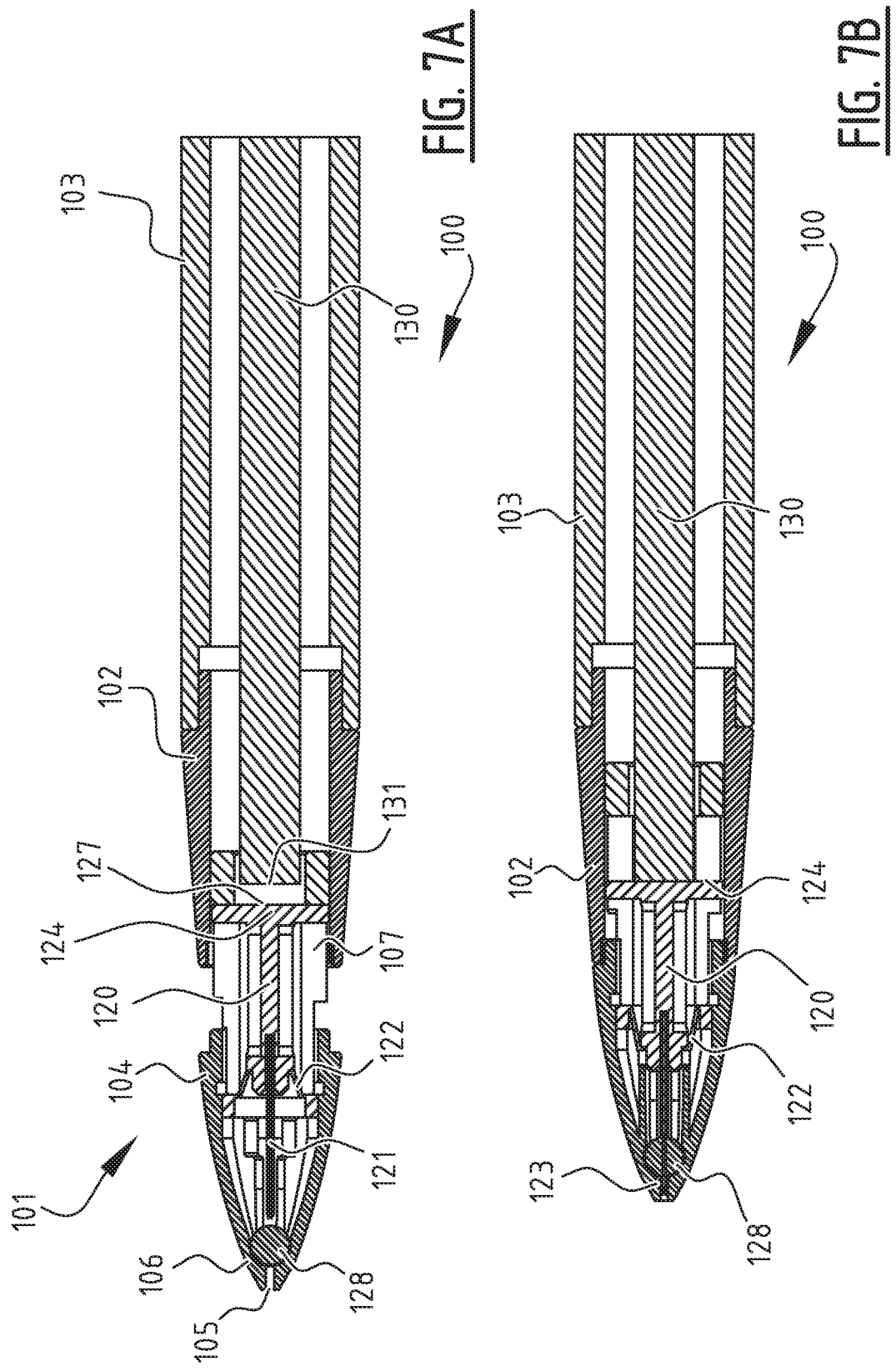

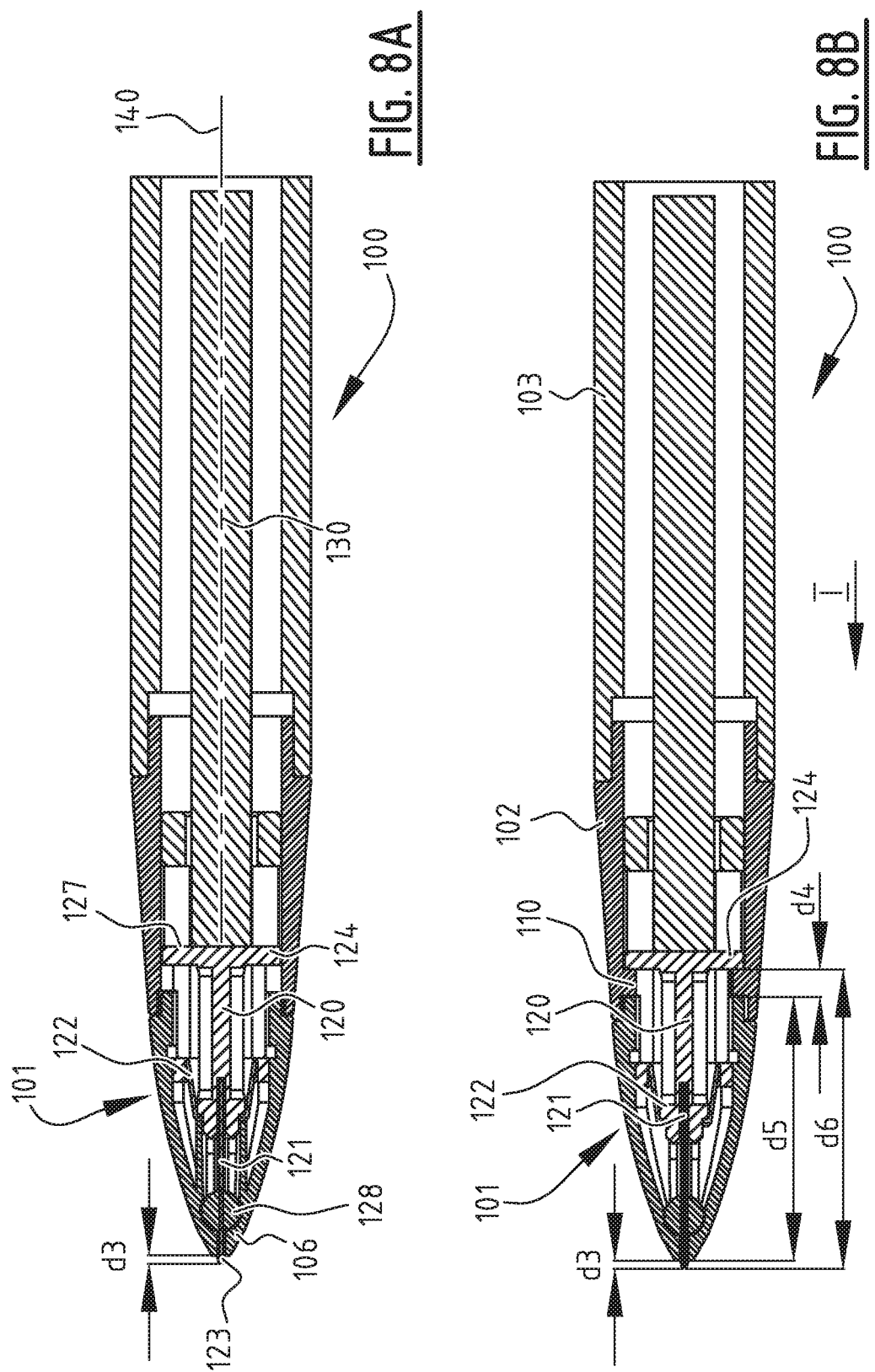

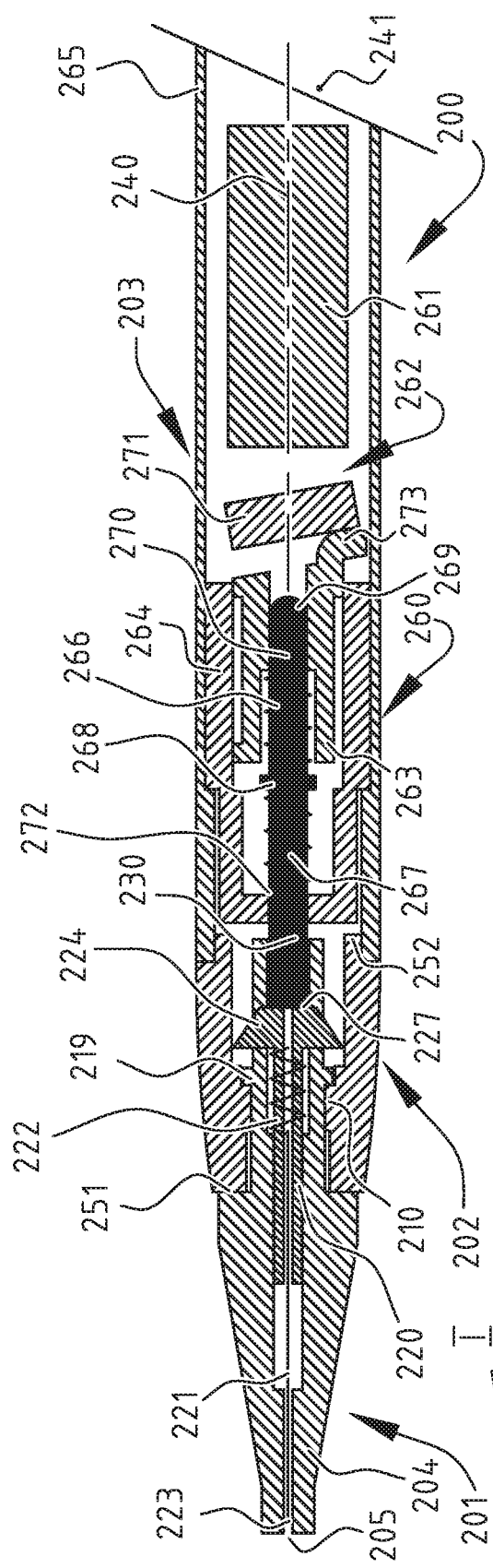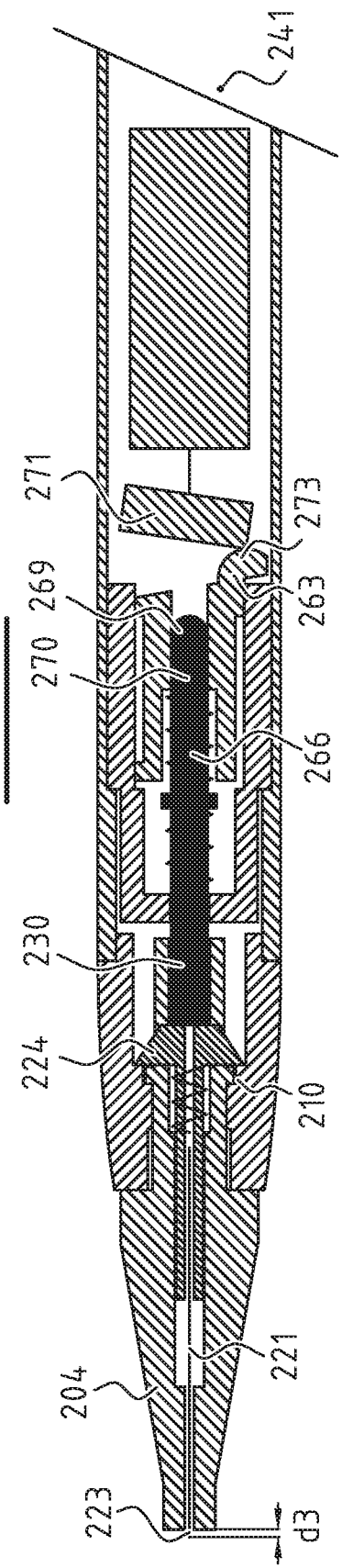
FIG. 10A
FIG. 10B

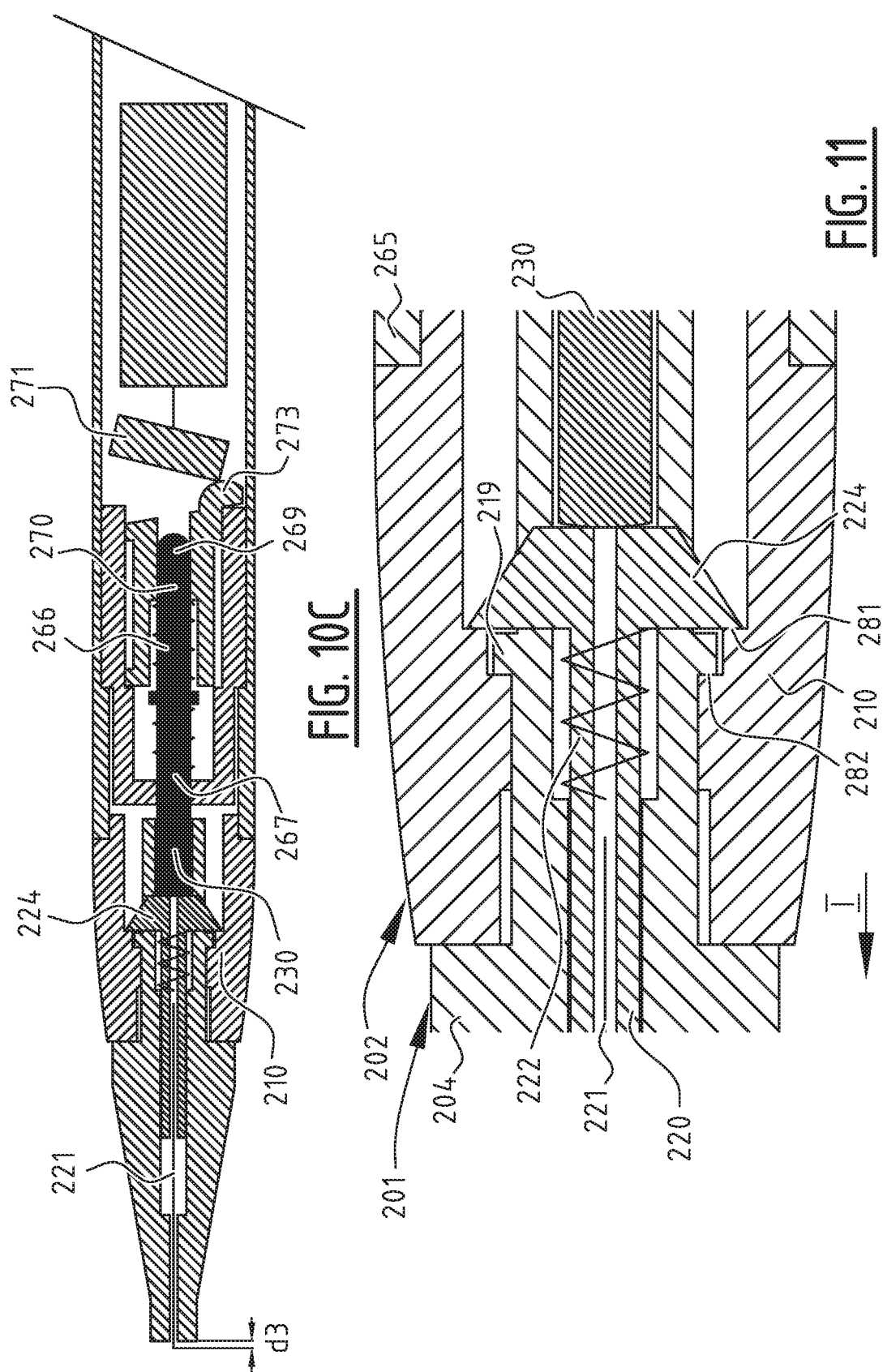

DEVICE AND NEEDLE MODULE FOR PUNCTURING SKIN

This is a national stage application filed under 35 U.S.C. § 371 of international application PCT/NL2018/050815, filed Dec. 6, 2018, which claims priority to Netherlands Patent Application No. NL 2020030, filed Dec. 6, 2017, Netherlands Patent Application No. NL2020710, filed Apr. 4, 2018, and Netherlands Patent Application No. NL2020818, filed Apr. 24, 2018, the entirety of which applications are hereby incorporated by reference herein.

The present invention relates to a needle module for puncturing skin and a device comprising a needle module for puncturing skin. The invention further relates to a method for introducing ink in the human skin.

In radiation therapy, or simply radiotherapy, a patient is typically locally subjected to a radiation beam to control or kill malignant cells. It is important that these beams are directed as accurately as possible onto the target to on the one hand ensure optimal therapy of these malignant cells and to on the other hand minimize damage to surrounding tissue upon exposure to the radiation beam.

To properly direct the radiation beams to the tissue as pre-operatively planned, it is known to apply small skin marks on the patient which can be used to automatically direct and align the beams as planned, for instance based on CT-scans of the patient. As radiation therapy typically involves subjecting the target to radiation beams repeatedly over time, sometimes several months, these marks need to remain during the course of therapy to ensure continued proper alignment. It is therefore known to introduce ink into the skin of the patient as skin mark.

Typically, for applying these marks, a small knife or scalpel is used. This knife is dipped in ink and subsequently introduced into the patient's skin. This can be a painful process, in particular in regions on the patient with superficial bone structures such as the thorax. Further, dipping the ink takes time and may result in accidental drips of ink, while at the same time accidental punctures due to the exposed knife are a risk.

Device for introducing ink in skin, for instance needle modules for puncturing skin in a reciprocal motion in accordance with the preamble of claim 1, are as such known from the field of tattooing or permanent makeup. Permanent marks are typically however not preferred by patients.

It is a goal of the present invention, next to other goals, to provide an improved and/or more efficient needle module for puncturing a skin wherein at least one of the above mentioned problems is at least partially alleviated.

This goal, amongst other goals, is met by a device according to appended claim 1. More specifically, this goal, amongst other goals, is met by a needle module for puncturing skin in a reciprocal manner, wherein the needle module comprises a needle unit, a housing and a biasing mechanism, wherein the needle unit comprises a needle, wherein said needle unit is movable with respect to said housing between an extended position wherein a distal end of the needle extends from a distal end of said housing and a retracted position wherein the distal end of the needle is positioned within the housing, wherein the biasing mechanism is arranged for urging the needle unit towards the retracted position, wherein the needle module further comprises a limiting mechanism, wherein the limiting mechanism is arranged for limiting the relative movement of the needle unit out of the distal end of the housing to a maximum extension distance when moving towards the extended position, wherein said maximum extension distance is 1.5 mm or less.

According to the invention, the needle unit is prevented to extend further from the housing than the maximum extension distance. This limits the insertion depth of the needle unit, more specifically the sharp distal end thereof, in the patient's skin to the maximum extension distance. The maximum extension distance may thus be defined as the maximum distance between the distal end of the needle unit and the distal end of the housing, from which the distal end preferably extends Preferably, the maximum extension distance is set to such a distance, that the needle unit, and therewith any ink, is only introduced in the epidermis of the patient's skin. Other than for instance in the field of tattooing, where the ink is introduced in the tissue underlying the epidermis, this will result in a non-permanent mark. It was however found that the superficial marks as applied using the needle module of the current invention remain sufficiently long to allow continued proper alignment during the course of radiotherapy.

The thickness of the layers of skin may vary between patients. Preferably, said maximum extension distance is 1.5 mm or less, even more preferably 1.2 mm or less, even more preferably 1.0 mm or less. The lower limit is defined such that the ink is introduced sufficiently deep in the skin and may for instance be 0.1 mm, preferably 0.2 mm. A preferred working range is between approximately 0.2 mm and approximately 0.8 mm.

Limiting the maximum extension further improves the safety of the needle module in use, which is, other than for instance in the field of tattooing and permanent makeup, of paramount importance in view of safety and conformity to medical safety standards.

According to a preferred embodiment, the limiting mechanism comprises mutually cooperating stop surfaces for limiting the relative movement of the needle unit and the housing. This provides efficient blocking of any further movement of the needle unit from the housing beyond the maximum extension distance. An efficient limiting mechanism is obtained if interior of the housing is arranged with protrusions and/or recesses for cooperating with protrusions arranged on the exterior of the needle unit.

Typically, a needle module of the kind according to the invention is coupled to a driving device which is provided with a driving rod which is driven, for instance by a suitable motor, in a reciprocal manner back and forth. Such a driving rod then engages the needle unit, thereby pushing the needle unit towards an extended position such that it extends from the housing. To urge the needle unit back upon withdrawal of the driving rod, the biasing mechanism then moves the needle unit back into the housing, i.e. towards the retracted position.

The needle unit is preferably arranged to move only along the longitudinal axis with respect to the housing. A rectilinear, reciprocal movement of the needle unit reduces any pain upon insertion of the needle unit in the patient's skin. To guide the needle unit in its rectilinear movement, it is preferred if a stop surface is substantially ring-shaped. For instance a ring-shaped stop surface may be arranged in the housing, through the opening of which the needle unit may be movable. The needle unit may then be provided with a cooperating stop surface, abutting the annular stop surface of the housing, thereby defining the maximum extension distance. These stop surfaces, or limiting mechanism more generally, then guide the needle unit with respect to the housing for ensuring in a rectilinear movement between the extended position and retracted position The biasing mechanism, for instance in the form of a spring or other elastic element, is preferably arranged to urge the needle unit back in the housing, for instance towards the retracted position. The biasing mechanism may be arranged between the needle unit and the housing to induce such a biasing force. In the case of a spring as biasing mechanism for instance, such a spring may be arranged between suitable protrusions arranged in the housing and the needle unit. As an alternative, an elastic element, for instance an elastic tubular member, may be fixed between the needle unit and the housing, wherein upon movement of the needle unit towards the extended position, the elastic member is elongated, thereby urging the needle unit backwardly when moving towards the retracted position.

According to a further preferred embodiment, the biasing mechanism engages the needle unit at a first location and wherein the needle unit is provided with a stop surface at a location at a distance from said first location. This separates the biasing means and the limiting mechanism, ensuring in a proper working of both of the mechanisms separately.

Preferably, the limiting mechanism is arranged to limit the movement of the needle unit with respect to the housing to such a distance, in which the biasing mechanism is not yet at its maximum relative movement. The biasing mechanism may for instance comprise a spring, against which the driving rod of a driving element works for moving the needle unit out of the housing. The limiting mechanism is then preferably arranged such that the biasing mechanism has not yet reached its end limit. For the case of the spring for instance, there may still be room between the windings of the spring. For the example of another elastic element, said elastic element may not yet be extended up to its final limits.

As an alternative, the maximum extension distance may be determined by the working range of the biasing means. Thus, according to a further preferred embodiment, the limiting mechanism is at least partially formed by the biasing mechanism, wherein the biasing mechanism is arranged for limiting the relative movement of the needle unit out of the distal end of the housing to said maximum extension distance. In this alternative, the maximum extension distance is determined by the biasing mechanism, i.e. the biasing mechanism limits the extension of the needle unit from the housing to the maximum extension distance. In other words, the biasing mechanism comprises, or forms, the limiting mechanism, such that, in the extended position, the biasing mechanism is at an end position.

According to a further preferred embodiment, the housing comprises a main housing part and a removable distal housing part. Such a module is easier to manufacture. Preferably, the main housing part and the distal housing part can be interconnected using a suitable removable interconnection, for instance a snap fit connection. It is hereby preferred if the limiting mechanism is at least partially arranged in the main housing part. This prevents accidental loosening of the distal housing part.

In order to improve the guiding action as already described above, it is then preferred if the main housing comprises a stop surface at or near the distal end. This improves the guiding action of the limiting mechanism as explained above as guiding the needle unit at the most distal part reduces any deflections of the more distal end of the needle unit.

As mentioned above, in particular the field of medical devices, safety plays an important role. In medical devices such as the needle module according to the invention, any risk to the use must be minimized. Therefore, according to a further aspect of the present invention, in the retracted position, the proximal end of the needle extends in the housing. As mentioned above, the proximal end of the needle unit is in use typically engaged by a driving rod of a driving device for pushing the distal end of the needle unit out of the housing. By providing a needle module wherein said proximal end is retained in the housing, and is preferably not accessible by hand from the outside of the housing, any accidental movement of distal end the needle unit out of the housing is prevented. This improves the safety in the resting or retracted position, that is when the device is not in use.

Preferably, the housing is substantially cylindrical, wherein the needle unit is movable within said cylindrical housing. The housing preferably has a length larger than the length of the needle unit, such that the needle unit can be completely received in said housing. Only upon coupling for instance a driving device, which is provided with a suitable driving rod which can be received in the proximal opening of the housing, the needle unit can be moved out of the housing.

By limiting on the one hand the maximum extension of the distal end of the needle unit and on the other hand preventing accidental punctures by ensuring that, in the retracted position, the proximal end of the needle extends in the housing, a needle unit which is safe to use is obtained. It should however be mentioned that the retention of the proximal end of the needle unit in the housing may also be applied to needle modules without a limiting mechanism as mentioned above or whereby the limiting mechanism allows for larger displacements than as mentioned before.

According to a preferred embodiment, the limiting mechanism is further arranged for limiting, in the retracted position, a displacement of the proximal end of the needle, such that the proximal end of the needle is retained in the housing. Suitable cooperating protrusions may again be provided to prevent any proximal movement of the needle unit from the housing. Also here, movement in the distal direction may be limited by the biasing means. The biasing mechanism may hereto be further arranged for retaining the proximal end of the needle in the housing.

Applying the skin marks using for instance the knife as described above takes time, as dipping the knife in a suitable coloring agent such as ink takes time. Ink in excess on the knife may further result in ink stains. In needle modules which are used in the field of tattooing or permanent makeup, the needle unit may comprise a plurality of needles in the needle unit. Although the risk of dripping is reduced using such a configuration, dipping the needle module, particularly the distal end of the needle unit, in the coloring agent still takes time.

Therefore, in a further improved needle module according to the invention, the housing is provided with a reservoir containing a coloring agent, such as ink, for introduction in said skin. As the coloring agent to be used is already available within the needle module, dipping said needle module in ink is no longer required. This further improves the process for applying a skin mark.

The coloring agent, or simply ink, is an agent which is suitable to be introduced in the human or animal skin. Preferably, the coloring agent is non-toxic and/or dermatologic neutral.

Preferably, the reservoir contains less than 0,3 ml of coloring agent, more preferably less than 0.1 ml. Other than for instance in the field of tattooing or permanent makeup, this is sufficient to apply the needed skin marks.

The reservoir is arranged for cooperation with the needle unit, in particular the distal end thereof, such that the coloring agent can be introduced in the patient's skin. To this end, it is preferred if the reservoir is arranged at or near the distal end of the housing. In case a two-piece housing for the needle module is used, comprising a proximal main housing part and a removable distal housing part, it is preferred if the distal housing part is provided with the reservoir. The distal housing part with reservoir can then be manufactured efficiently or even replaced if required.

With a reservoir extending at or near the distal end of the housing the coloring agent can be efficiently transferred to the distal end of the needle unit, for instance through capillary forces. To improve the transfer of coloring agent to the distal end of the needle unit, it is preferred if, according to a further preferred embodiment, the distal end of the needle unit is reciprocally movable between a position near and away of the reservoir when moving between the retracted and extended position. In the position near the reservoir, coloring agent can be transferred, for instance by capillary forces, to the distal end, wherein in the position away or in the extended position, said ink can be transferred to the skin. Coloring agent transfer is further improved if the distal end of the needle unit is reciprocally movable in and out of the reservoir when moving between the retracted and extended position. In use, when driven by a suitable driving device, the distal end is thus moved between a position within the reservoir, allowing efficient ink take-up, to the position wherein the distal end extends from the housing, for introducing said ink in the patient's skin.

According to a further preferred embodiment, the distal end of the needle unit extends at a proximal distance from the reservoir in the retracted position. The needle unit is then at a distance form the reservoir, preventing any spillage of the coloring agent.

Upon use of the needle module, said module is typically coupled to a driving device having a reciprocally movable driving rod. According to a further preferred embodiment, upon coupling the needle module to a driving device, the needle unit is movable to an intermediate position, said intermediate position being located between the extended and retracted position and wherein the needle unit extends within the reservoir. Upon coupling the needle module, the needle unit, preferably the distal end thereof, is moved distally and is received within the reservoir. Coloring agent can thus be transferred to the needle unit prior to use. In use, the needle unit is then moved between the intermediate position and the extended position.

Preferably, the reservoir is retained by the housing. The reservoir may for instance be formed by two films for holding there between the coloring agent. The films may be pierced by the distal end of the needle unit prior to use. Preferably, the housing further comprising a first film arranged near the distal end of the housing and a second film arranged further from the distal end and wherein the reservoir is positioned between the first and second film.

It is noted that although the use of a reservoir in the housing has advantages in terms of safety, after all, separate dipping of the ink is no longer required, and thus also helps in improved the safety of the device, as do the aspects of the limiting mechanism and the proximal end of the needle unit in the housing, the aspect of the reservoir in the housing can also be applied in a needle module as such, for instance as specified by the preamble.

According to a further preferred embodiment, the reservoir comprises a cartridge for holding the coloring agent, wherein the cartridge can be punctured by the needle and wherein the housing is arranged for holding the cartridge. By providing the coloring agent in the cartridge an easier assembly process is obtained as one does not have to work with the separate fluid during assembly of the needle module, which could lead to spills and contamination. Thus, the cartridges can be processed in a manner similar to processing the remainder of the needle module parts or components during assembly. Preferably, the cartridge is a removable cartridge. Hereby, it is made easier to change a cartridge in the needle module, such that one can for instance change the cartridge to a cartridge that contains a different type or coloring agent or a cartridge comprising a different color of coloring agent.

The limiting mechanism is arranged to limit the maximum extension of the needle from the housing. However, typically a driving device, which may be provided with a driving rod for reciprocally driving the needle unit, is only arranged to reciprocate between predetermined maxima. Therefore, a further preferred embodiment of the device further comprises a decoupling mechanism for reciprocally driving the needle unit between the retracted and the extended position, wherein the decoupling mechanism comprises a first end arranged to be driven reciprocally and a second end arranged to drive said needle unit, wherein the first and second ends are movable relative to each other, wherein the first end is reciprocally movable with a first amplitude of displacement and wherein the second end is movable with a second amplitude of displacement being smaller than the first amplitude of displacement. Thereby the decoupling mechanism is arranged for allowing an at least partly decoupled motion of the needle unit with respect to the driven end of the decoupling mechanism, such that if a motion of the needle unit is restrained or blocked by the limiting mechanism, the decoupling element is arranged to absorb the reciprocal motion that is applied on the driven end of the decoupling mechanism.

Preferably, the decoupling mechanism further comprises biasing means arranged for urging the first and second ends apart and/or the decoupling mechanism comprises a first part comprising said first end and a second part comprising said second end, wherein said first part and second parts are movable relative to each other and wherein biasing means are arranged between the said first and second parts for urging said ends apart. Due to this, the biasing means ensure that the first and second parts move together in a synchronized manner when movement of the second end, hence the second part, is not blocked by the limiting mechanism or other blocking means. Hence, a driving mechanism, such as a reciprocating linear motor that has a single length of stroke, can be used for driving a needle unit with a smaller length of stroke.

The decoupling mechanism is provided in the needle module, according to a further preferred embodiment, wherein the first end of the decoupling mechanism is arranged to cooperate with a driving rod of a driving device. Hereby a simple driving device which does not comprise a decoupling unit, such as for instance used for tattooing, can be used for driving the needle module, wherein the maximum extension distance of the distal end of the needle can be set independently of the length of the reciprocating stroke of the driving device. The driving rod then drives the first end of the decoupling mechanism, which is provided as part of the needle module.

The invention further relates to a device for puncturing skin, comprising a driving device and a needle module according to the invention, wherein the driving device comprises a motor for reciprocally driving a driving rod for reciprocally moving the needle unit. The driving device is preferably arranged to engage the proximal end of the needle unit, which may be retained in the housing as mentioned above. The driving device is thus shaped accordingly. Hereby the needle can be driven continuously in a reciprocating manner for sustained amounts of time.

If an ink reservoir is arranged in the housing of the needle module, in particular a distal end thereof, it is preferred if the needle module is arranged such that, upon mounting of the needle module onto the driving device, the distal end of the needle is moved to the intermediate position. More preferably, the needle module is arranged to move the distal end of the needle in a range between the intermediate position and the extended position. As mentioned above, this allows and efficient ink take-up from the reservoir.

It is then preferred if the motor is coupled to the needle unit through the decoupling mechanism arranged between the motor and driving rod, wherein the second end receives the driving rod. As mentioned above, this allows for using a driving device comprising a motor and/or drive mechanism for generating a reciprocal motion with a single length of stroke.

More preferably, the decoupling mechanism is provided in the driving device. Providing the decoupling mechanism in the driving device, allows for the use of simpler needle modules. As the needle modules are intended for single usage, the production costs and efforts of these disposable needle modules are reduced.

In a further preferred embodiment the limiting mechanism is at least partly provided on the needle module and partly provided on another part of the device, different from the needle module, and wherein the limiting mechanism is arranged such that, when the needle module is in a coupled state with the driving device, the maximum extension distance is less then the maximum extension distance in an uncoupled state of the needle module. Hence, the limiting mechanism is made up from different cooperating parts that are arranged on the different modules and/or parts of the device, for instance a stop surface that is arranged in the needle module and a stop surface, provided on another part of the device that is arranged to come into contact with the stop surface on the needle module. Hereby, the maximum extension distance is determined by the assembly of the different modules of the device, such that, for instance, a standard needle module can be used with different driving devices for setting a distance that the needle is allowed to extend from the tip of the housing of the needle module. Thereby only a single needle module is needed with a simple design, which can be manufactured cheaply in bulk.

A further preferred embodiment of the device according to the invention further comprises a spacer for setting the extended position of the needle unit, wherein the spacer is arranged between the driving device and the needle unit for adjusting the relative position of the housing and the driving rod of the driving device. This allows fine-tuning the extended position of maximum extension of the distal end of the needle unit from the housing. Preferably however, this maximum extension is limited by the limiting mechanism as mentioned above. The spacer then allows further limitation of the maximum extension distance by introducing a separate part, i.e. the spacer, between the needle module and the driving device. This will change the relative position of the driving device and the needle module and therefore also the reciprocal working stroke of the driving rod.

According to an aspect of the invention, the device is provided with a limiting mechanism. An efficient and compact configuration is obtained if this mechanism is arranged in the needle module. The needle module may thereto be provided with the cooperating stop surfaces.

It is however also, or additionally, possible that the limiting mechanism comprises mutually cooperating stop surfaces arranged on the needle unit and the spacer, for limiting a relative movement of the needle unit and the housing. The maximum extension of the tip of the needle can thereby be determined by the placement of the stop surface on the spacer. This allows for the use of a single design for the needle module, in combination with different spacers, for setting different maximum extension differences. In addition, this reduces the amount of parts that need to be fabricated with strict and precise tolerances. For instance, by forming the limiting mechanism on the coupled spacer and needle module, the driving device as such has a negligible influence on the precision with which the needle is allowed to extend from the tip of the housing in its maximum extension.

Preferably, the spacer is provided with a blocking surface comprising a stop surface which cooperates with a stop surface of the needle module for forming a bayonet connection, or a similar type of form-locked connection, between said spacer and said needle module, wherein said blocking surface of the spacer further comprises a stop surface of the limiting mechanism for limiting a relative movement of the needle unit and the housing. By employing the blocking surface of the spacer for locking the needle module to the space, but also using the same blocking surface as a part of the limiting mechanism, the number of features that have to be fabricated onto or within the spacer are reduced. The reduced complexity obviously reduces production costs, but also eliminates a component in the stacking or sum of uncertainties due to production tolerances, thereby enabling a higher precision in setting the maximum extension distance of the needle distal end.

In a further preferred embodiment, an outwardly extending protrusion is provided on the needle unit, a guide is arranged in the housing for guiding said outwardly extending protrusion and wherein said outwardly extending protrusion comprises the stop surface of the needle unit. The needle unit according to this embodiment is allowed to displace within the housing of the needle module up to the point where the stop surface contacts a mutually cooperating stop surface provided on a part of the device being different from the needle module, such that it can extend no further. In this process, the protrusion is guided in the guide in the housing to ensure a smooth operation of the mechanism.

In a further preferred embodiment the spacer is provided with an inner wall, which is arranged on an inner circumferential surface, near a distal end, of the spacer and wherein said blocking surface is provided on the inner wall. It is further preferred that the limiting mechanism comprises said stop surface arranged on the outwardly extending protrusion on the needle unit and said blocking surface arranged on the inner wall of the spacer and wherein said blocking surface is arranged to abut said stop surface when the distal end of the needle is at its maximum extension distance. By controlling the placement of this inner wall within the spacer with respect to the distal end of the spacer, one allows for controlling the extension distance of the needle. Thereby the sources of uncertainty for the resulting extension distance are limited to the dimensioning of the inner wall with respect to the distal end of the spacer, the length of the housing of needle module and the distance between the needle tip and the stop surface arranged on the needle unit.

In a preferred embodiment the device is arranged such that the needle module, spacer and/or driving device can be interconnected by means of a bayonet connection. Bayonet connections allow for reliable, but easy to use connections between the different parts, which typically do not require the use of tools or training to operate.

The bayonet connection preferably comprises first locking means for locking a relative longitudinal movement of the interconnected needle module and spacer. It is more preferred if the first locking means comprise the blocking surface on the spacer and a locking surface on an exterior of the housing of the needle module, wherein the locking surface is arranged at a part of the housing that is arranged to be inserted into the spacer. It is even more preferred if the limiting mechanism and the first locking means comprise the blocking surface on the spacer. Hereby, the needle module and spacer can be connected in a reliable manner, such that the spacer and needle module are in the same relative position with respect to each other. If the blocking surface on the spacer is used for locking the relative movement between the needle module and the spacer, the two components are fixed in the same manner at known relative position, such that the maximum extended distance of the needle tip is accurately determined.

In a further preferred embodiment the bayonet connection comprises second locking means for locking a relative rotational movement of the interconnected needle module and spacer. Preferably, the second locking means comprise a protrusion and/or recess provided on the exterior of the housing at the part of the housing that is arranged to be inserted into the spacer and wherein a matching protrusion and/or recess is provided on an interior of the spacer, which are arranged for forming a snap-fit connection. More preferably said protrusion and/or recess provided on the exterior of the housing passes said matching protrusion and/or recess provided on the interior of the spacer to lock or unlock the snap-fit connection and wherein at least one of the housing and spacer deforms to allow for the passing. This minimizes the risk that the bayonet connection accidentally loosens, whereby the needle module can disengage from the spacer, or reduce the accuracy of setting the maximum extended distance of the needle tip. A snap-fit connection has the benefit of creating a reliable connection that is easy to open and close. In addition, as it "snaps" when it locks, the operator gets the confirmation that the connection is secured.

According to a further preferred embodiment, the device consists of nonmagnetic parts. This may apply to the needle module as such, any spacer, any driving device and the respective parts thereof. This allows the device to be used near a scanner such as a MRI scanner. The device preferably does not contain any (ferro)magnetic materials, at least not to such an extent which renders the device unsuitable to be used in close proximity to for instance a MRI scanner.

The needle may for instance be manufactured from a nonmagnetic material, such as titanium or aluminium. Also other parts, for instance any biasing mechanism, may be manufactured from this such a material. Other parts, such as the housing, may be manufactured from a plastic. The device preferable does not contain any electronic components. A suitable motor for the driving device is for instance a pneumatic motor. Other non-electric motors may be used as well.

It is noted that the aspects of the interconnectability of the different devices and modules by means of the bayonet connection, or partly decoupling the motion of the reciprocal drive and needle unit by means of the decoupling device and spacers for adjusting the relative position of the housing and the driving rod of the driving device can also be applied in a needle module as such, for instance as specified by the preamble, or a device comprising a needle module as such.

The invention further relates to a kit of parts comprising the device, the needle module and a plurality of spacers for setting different predetermined distances as mentioned above, wherein the respective spacers are arranged to define varying respective extended positions. Preferably, the spacers have varying lengths, for instance with respective difference of at least 0.1 mm, preferably at least 0.2 mm, more preferably at least 0.5 mm. The respective extended positions then preferably mutually vary at least 0.5 mm. The kit of parts preferably also comprises the driving device.

The invention further relates to a method for introducing ink in the human skin, in particular for applying a skin mark on a patient, comprising the steps of:
providing a device as described above;
providing a coloring agent; and
driving the needle in a reciprocating manner for puncturing the human skin and depositing the coloring agent using the needle in an upper layer of the skin.

The present invention is further illustrated by the following Figures, which show a preferred embodiment of the device and method according to the invention, and are not intended to limit the scope of the invention in any way, wherein:

FIG. 1 schematically shows a needle module in perspective;

FIGS. 2a and b show an embodiment of the needle module in cross-section with the needle unit in retracted and extended position;

FIGS. 3a-c show another embodiment of the needle module in cross-section with the needle unit in different positions; and FIGS. 4a-d show another embodiment of the needle module;

FIGS. 7a and b show the embodiment of the device in cross-section before mounting of the needle module and after mounting, wherein the distal end of the needle is in the intermediate position;

FIGS. 8a and b show cross-sections of the embodiment, wherein the distal end of the needle is in the extended position.

Figure 9A:
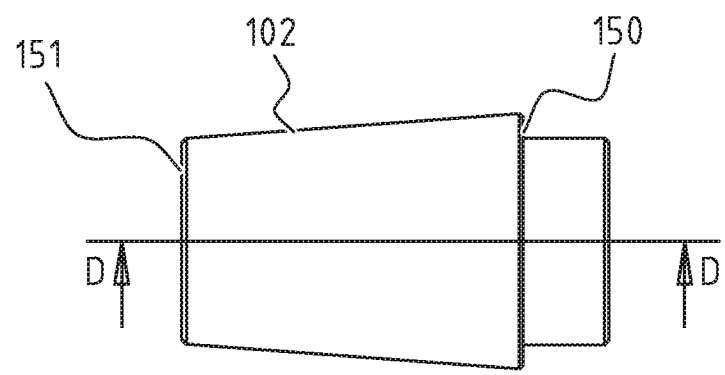

FIGS. 9a, b and c show the spacer of FIGS. 5-7c in different views;

FIGS. 10a, b, and c show an embodiment of the device, whereby the driving device comprises a motor, in cross-section for different snapshots of a reciprocal movement cycle of the needle unit;

FIG. 11 shows in more detail the limiting mechanism, according to the embodiment of FIG. 10, in cross-section.

Figure 1:
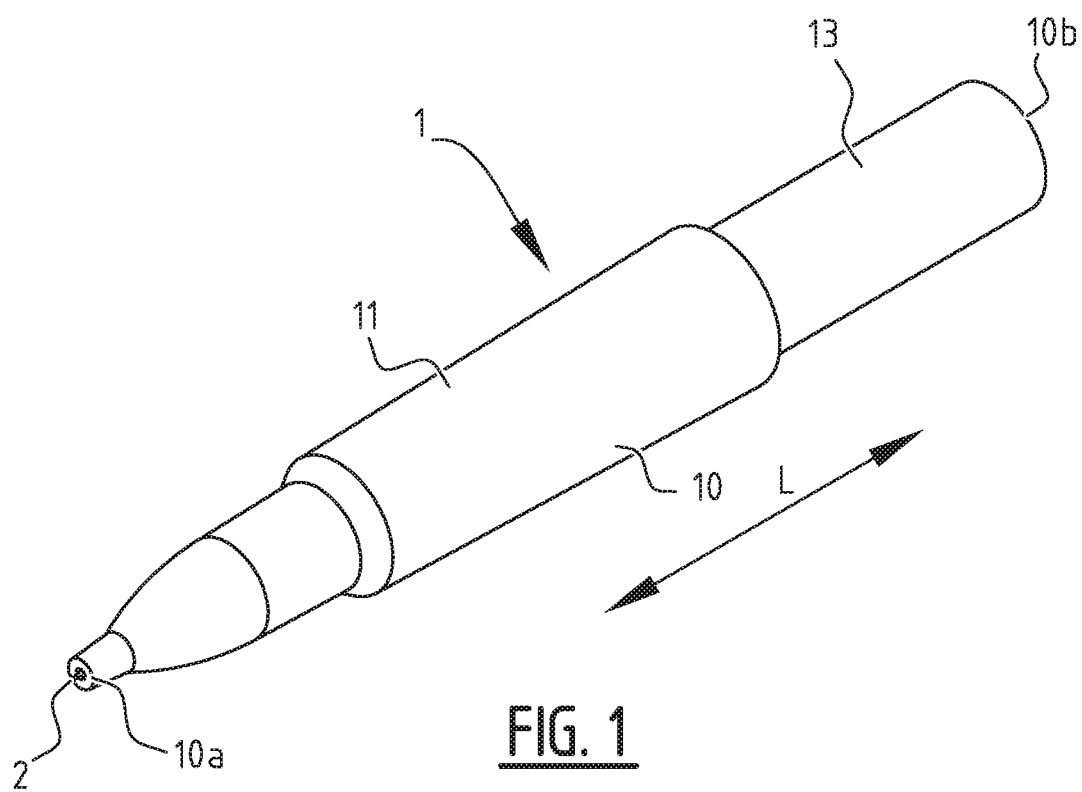

In FIG. 1, a needle module 1 for coupling to a driving device (not shown) such as a tattooing gun or permanent makeup device is shown. The needle module 1 comprises a housing 10, which is in this example substantially cylindrical. The housing 10 comprises an open proximal end 10b (see also the cross-sections of FIGS. 2a and b) and an open distal end 10a. The proximal end 1-b is arranged to couple with the driving device (as will be explained in in relation to FIGS. 3*a*-*c*) and is thereto in this example provided with a area 13 of reduced diameter. The step 13*a* may function as stop surface and determines the relative position of a coupled driving device and the needle module 1. The housing 10 in this example is further formed by two separate housing parts 11 and 12. The distal housing part 12 is provided with a tapering distal end 10*a* and can be coupled to the proximal main housing part 11 through a snap-fit connection, generally indicated with 12*a*.

Through the distal end 10*b* of the housing 10, a needle unit 2 may be extended. The needle unit 2 (see FIG. 2*a*) comprises a needle base 23, in this example of a rigid plastic, and a needle 21 at its distal end. The distal end 22 of the needle 21 is sharp. In this example, the needle unit 2 is provided with a single needle 21. It is however also possible to provide a plurality of needles 21, see for instance the embodiment of FIGS. 4*a*-*d*. The needle module 1 is arranged such that the needle unit 2 is reciprocally movable along its longitudinal direction L with respect to the housing 10 between a retracted position wherein the distal end 22 of the needle unit 2 extends in the housing 10 (see FIG. 2*a*) and an extended position wherein the distal end 22 of the needle unit 2 extends from the distal end 10*a* of the housing (see FIGS. 1 and 2*b*).

The movement of the needle unit 2 out of the housing 10 in the distal direction D is induced by the movement of a driving rod 32 (see for instance FIG. 3*b*) of a driving device 3. Said driving device 3 is arranged to reciprocally move the driving rod 32 with a predetermined amplitude along the longitudinal direction Lb. The movement of the needle unit 2 back into the housing 10 is induced a biasing mechanism 4 which comprises a spring 41 in this example. The biasing mechanism 4 extends between the housing 10 and the needle unit for urging the needle unit 2 towards the retracted position. In this example, the spring 41 is arranged between a stop surface 11*a* of the housing 10, formed on the inner surface thereof in this example, and a stop surface of the needle unit 2, in the example the base 23 thereof. The spring 41 will urge the needle unit 2 proximally in the direction P with respect to the housing, i.e. towards the retracted position.

In the distal direction D, the relative movement between the needle unit 2 and the housing 10 is limited by a limiting mechanism, in this example in the form of cooperating protrusions 11*c*, 23*b* of the housing 10, respectively the needle unit 2. The protrusion 11*c* and 23*b* are abutting in the position as shown in FIG. 2*b*. In this example, the protrusion 11*c* is arranged on the inner wall of the housing 10, more specifically the most distal part of the main housing part 11. The protrusion 11*c* further serves to guide the needle unit 2 to only move in the longitudinal direction and is thereto preferably ring or annular shaped. The protrusion 23*b* of the needle unit 2 is arranged on the relative rigid base part 23. The limiting mechanism limits the extension of the needle unit 2 from the housing 10 to a maximum extension, schematically indicated with the distance d in the detail of FIG. 2*b*. The distance d is the distance between the distal end 22 of the needle unit 2 and the distal end 10*a* of the housing 10. In this example, the maximum extension is defined as 1.2 mm. This ensures that in use, the needle point 22 will only be inserted into the epidermis of the patient.

From FIG. 2*b*, which shows the needle unit 2 in the most distal position possible, it can be seen that the spring 41 is not in its complete compressed position. The relative movement between the needle unit 2 and the housing 10 is thus not limited by the biasing mechanism. As an alternative, the biasing mechanism may also form the limiting mechanism in the sense that the final position of the biasing mechanism (for instance the spring in completely compressed situation) limit the maximum extension, in this example set at 1.2 mm as mentioned above.

In the example shown, the protrusion 23*b* of the limiting mechanism formed on the needle unit 2 extends at a distance from the protrusion 23*a* operating with the biasing mechanism. The biasing mechanism thus engages the needle unit 2 at a first location and wherein the needle unit 2 is provided with a stop surface 23*b* at a location at a distance from said first location.

The movement in proximal direction P of the needle unit 2 with respect to the housing 10 is limited by a stop surface 11*b*, in this example formed by a separate plastic or rubber ring shaped element 11*b*. The ring 11*b* further serves to guide the needle unit 2 to only move in the longitudinal direction. In the retracted position as shown in FIG. 2*a*, the needle unit 2, in this example the same protrusion 23*a* operating with the spring 41, abuts the protrusion 11*b* of the housing 10. From FIG. 2*a*, which shows the needle unit 2 in the most proximal position with respect to the housing 10, it is clear that also in this retracted position, the proximal end 24 of the needle unit 2 is completely retained or received in the housing 10. In this example, the proximal end 24 extends at a distance from the proximal end 10*b* of the housing 10. As the proximal end 24 extends in the housing 10, the proximal end 24 cannot be accidentally, for instance due to manual operation, moved to extended position.

The embodiment as shown in FIGS. 2*a*-*b* can be used for applying a skin mark to a patient by dipping the distal end 22 of the needle unit 2 in an ink reservoir (not shown) and to subsequently apply the device to the patient. In the embodiment as shown in FIGS. 3*a*-*c* however, the needle module 1 is provided with an ink reservoir 5 near the distal end 10*a* thereof. In this example, the ink reservoir 5 is arranged near the distal end 10*a* of the distal housing part 12. The reservoir 5 is formed by two films 51, 52 arranged at a mutual distance, between which suitable ink 53 is arranged to be applied on the patient's skin.

In the retracted position as shown in FIG. 3*a*, the distal end 22 of the needle unit 2 extends at a distance proximally from the reservoir. The needle unit 2 does not extend in the reservoir 5 as can be seen. Only when the needle module 1 is coupled to a driving device 3, the needle unit 2 will be moved distally such that the needle unit 2 will extend in the reservoir 5. This is visible in FIG. 3*b*. Ink 53 from the reservoir will be transferred to the needle unit 2, in particular the distal end 22 thereof. In this example, the distal end 22 extends distally from the most distal end of the reservoir (in this example formed by the film 52) as can be seen in the detail of FIG. 3*b*. It is however also possible that in this position, the distal end 22 of the needle unit 2 extends in the reservoir for efficient ink take-up.

It is hereby noted that driving device 3 is provided with reciprocally movable driving rod 32, which is movable between an inner position (FIG. 3*b*) and an outer position (3*c*). Upon coupling of the driving device 3, the needle unit 2 will be moved from the retracted position (FIG. 3*a*) to an intermediate position (FIG. 3*b*). In this position, the needle module 1 is ready for use. In use, the driving rod 32 will be reciprocally driven between the inner (FIG. 3*b*) and outer positions (FIG. 3*c*). In the outer position of the driving rod 32, the needle unit 2 will be urged distally such that the distal end 22 of the needle unit 2 protrudes from the distal end 10*a* of the housing 10. With reference to FIG. 3*c*, it can be seen that the limiting mechanism is not yet operative, i.e. the protrusions 11*c* and 23*b* are not yet in contact. The extension $d_2$ of the distal end 22 of the needle unit 2 from the distal end 10a of the housing 10 is in this example determined by the outer position of the driving rod 32, i.e. the amplitude thereof. The distance $d_2$ is smaller than the distance d as shown in FIG. 2b. The limiting mechanism in FIG. 3c here functions as safeguard to ensure that the maximum extension is not exceeded.

The distance $d_2$ is determined by the relative position of the needle module 1 and the driving device 3. This relative position can be adjusted by exchanging a spacer 6 with a different space 6 having a different length e. Ring shaped spacer 6 abuts the step 13a provided in the housing 10 to ensure a proper relative potion of the needle module 1 and the spacer 6. It will be appreciated that by arranging a larger spacer 6 (in terms of length e), the distance $d_2$ will decrease.

Figure 4A:
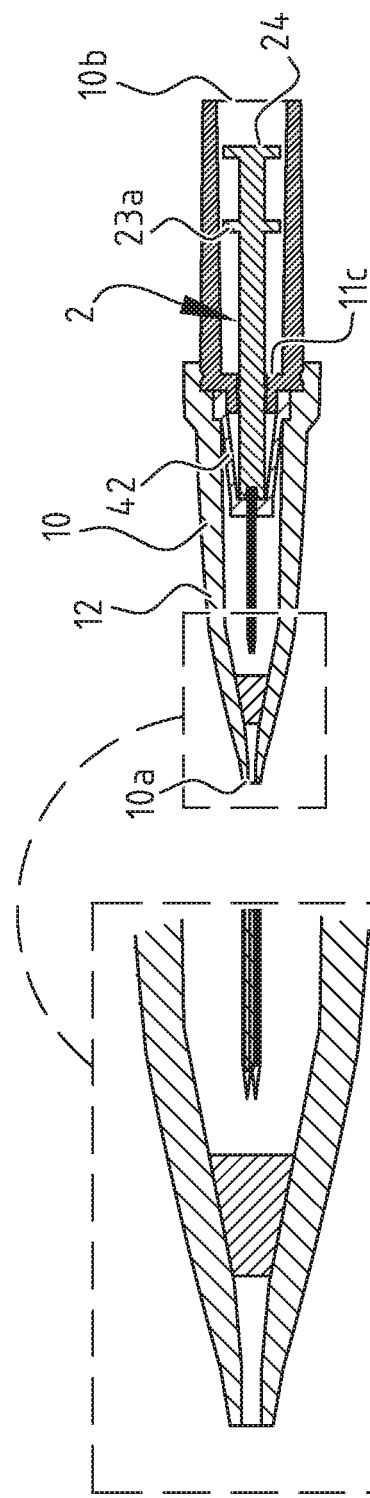

As an alternative to the spring 41 as biasing mechanism, the embodiment of FIGS. 4a-d is provided with an elastic element 42 for urging the needle unit 2 back to the retracted position as shown in FIG. 4a. Also in this position, the proximal end 24 of the needle unit 2 is retained in the housing 10.

The elastic element 42 is in the form of an elastic tube, which is connected to the housing 10, in this example at the interconnection between the distal housing part 12 and the proximal housing part 11. The other end of the elastic element 42 is connected to the needle unit 2 at the distal location, in this example at the distal end of the base 23. It will be appreciated that the elastic properties of the element 42 will urge the needle unit 2 back from the position as shown in FIG. 4b to the position as shown in FIG. 4a.

Figure 4B:
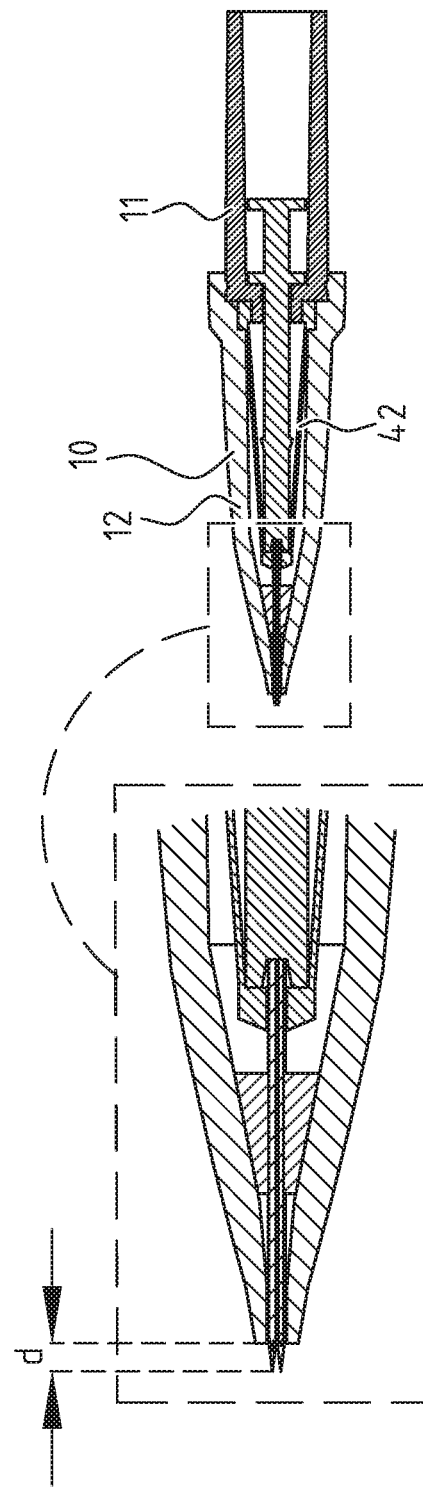
Figure 4C:
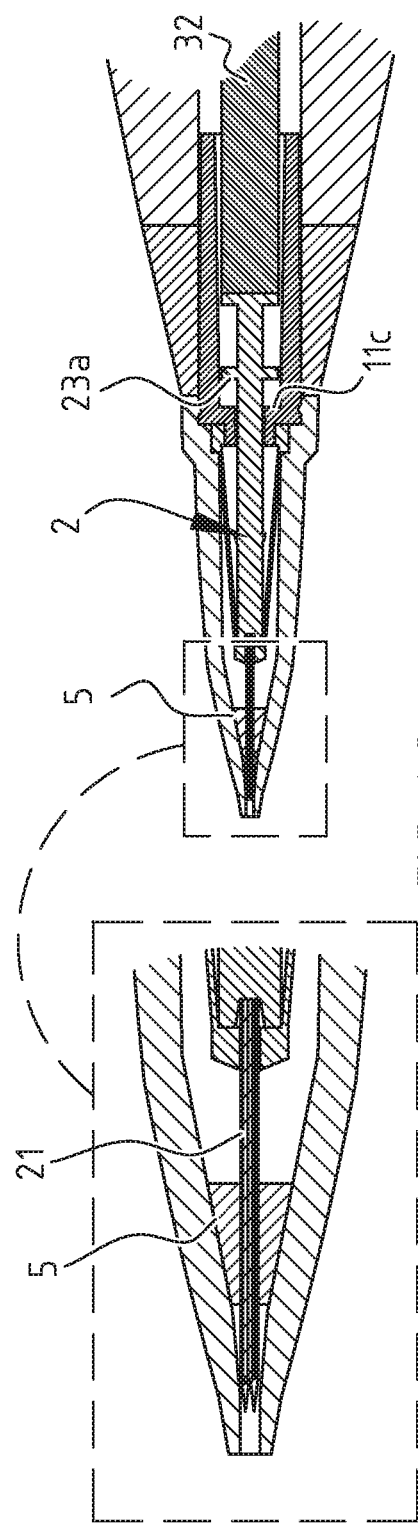

Also in this embodiment, a limiting mechanism in the form of cooperating protrusions 23a and 11c is provided to limit the extension of the needle unit 2 from the distal end of the housing 10 to a maximum extension d (see the detail of FIG. 4b).

Figure 4D:
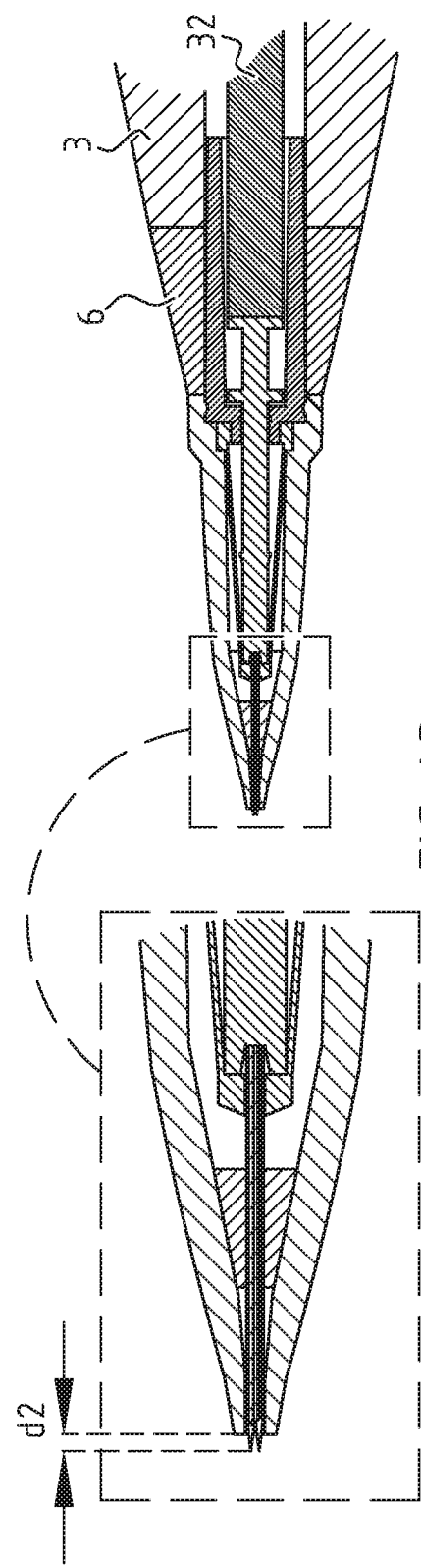

With reference to FIGS. 4c and 4d, it will again be appreciated that upon mounting the needle module 1 to a combination of a driving device 3 and spacer 6, the needle unit 2 will be urged into the ink reservoir 5. Driving the driving rod 32 will reciprocally move the distal end 22 of the needle unit 2, which is provided with a plurality of needles 21, between the intermediate position (FIG. 4c) and the extended position (FIG. 4d). Again, in FIG. 4d the protrusions 11c, 23a of the limiting mechanism are not yet in abutment, such that the extension distance $d_2$ is again smaller than the maximum distance d. The distance $d_2$ is again determined by the length of the spacer 6.

Figure 5:
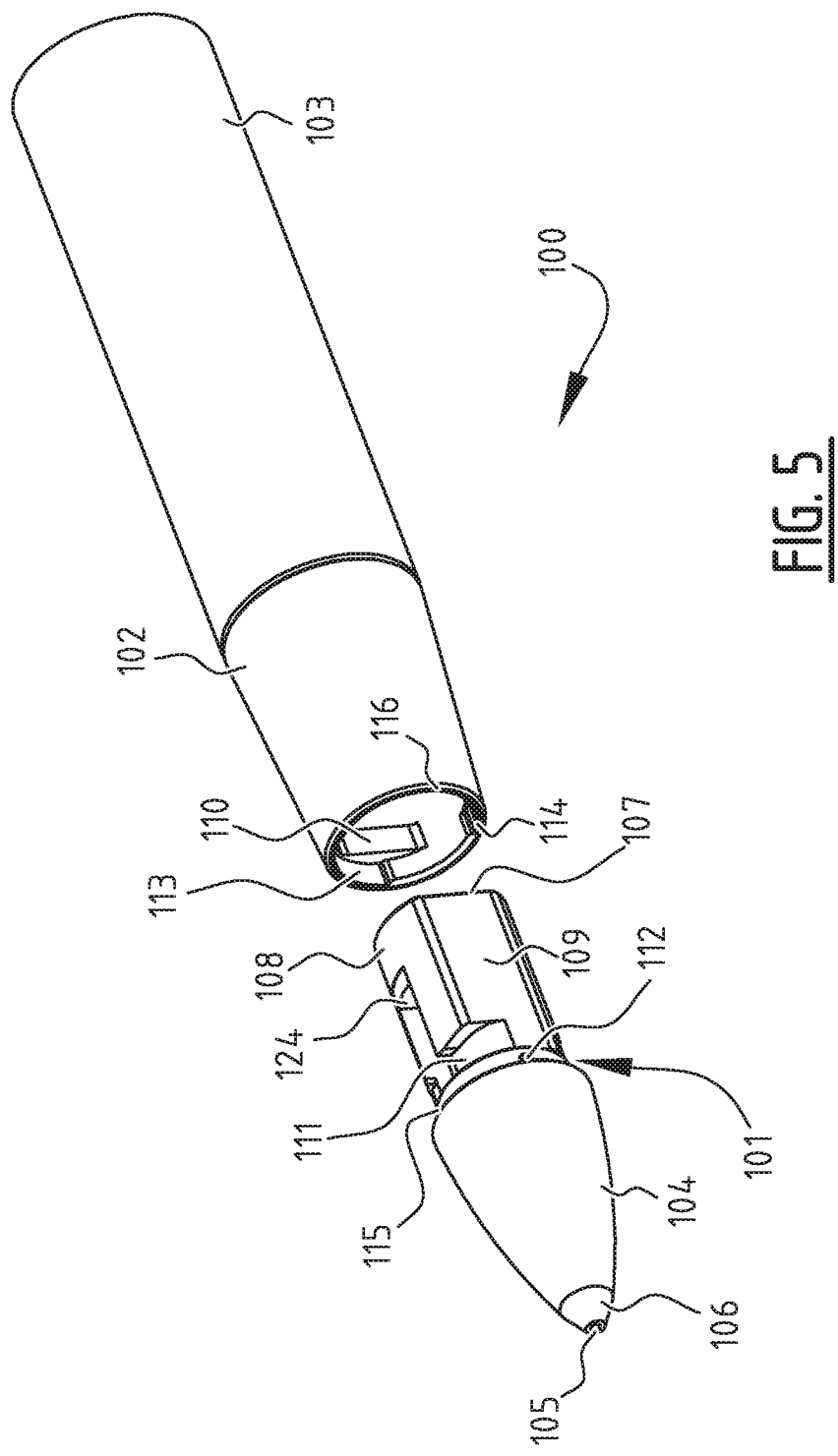
FIG. 5 shows an embodiment of the device comprising a needle module, a spacer and a driving device in perspective view.

FIG. 5 shows a further embodiment of the device 100 comprising a needle module 101, a spacer 102 and a driving device 103 in perspective view. The needle module comprises a distal housing part 104, with an opening 105 for the needle positioned in its tip 106. The main housing part 107 is mounted to the distal housing part 104 through a snap-fit connection, whereby these two housing parts 104, 107 form the housing of the needle module. The main housing part 107 has circular shaped sections 108 and rectangular shaped sections 109. This shape of the main housing 107 matches with the internal space of the spacer 102, more specifically with the inner retaining walls 110 of the spacer. The inner retaining wall 110 is comprises a protrusion, which is arranged at a part of the internal circumference of the spacer 102. By aligning the needle module 101 correctly with the spacer 102, the needle module 101 can be inserted into the spacer 102 by a longitudinal movement, whereby the rectangular shaped sections 109 pass the inner retaining wall 110 of the spacer 102. Following the longitudinal movement for inserting the main housing part 107 in the spacer 102, the needle module can be rotated, with respect to the spacer 102, (in this example clockwise) around its longitudinal axis, whereby the inner retaining wall 110 interlock in the matching cavities 111 of the main housing part 107 and the needle module 101 is locked in longitudinal direction in the spacer 102. Note that the needle module 101 can also be constructed, such that is can be coupled through a counterclockwise rotation. Such a connection is often referred to as a bayonet connection. Small protrusions 112 are arranged on the housing of the needle module 101, which cooperate with circumferential recesses 113 located in the circumferential wall on the inside of the spacer 102 near the spacer's distal end. Upon insertion of the needle module 101 into the spacer, an edge 115 at the side of the distal housing part 104 opposed from the tip is arranged to abut a matching edge 116 provided at the distal end of the spacer 102. Thereby, the small protrusions 112 are inserted in recesses 113. By rotating the needle module 101 as described above, the protrusions are locked in place, by a snap-fit connection formed at a first end 114 of the recesses 113. Thereby, a simple and reliable connection between the spacer 102 and the needle module 101 is obtained. After use, the snap-fit connection can be opened by applying a torque on the needle module 101 in the opposite direction (counterclockwise), after which the needle module 101 can be released from the spacer 102 by a (counterclockwise) rotation and extraction of the needle module 102.

Figure 6:
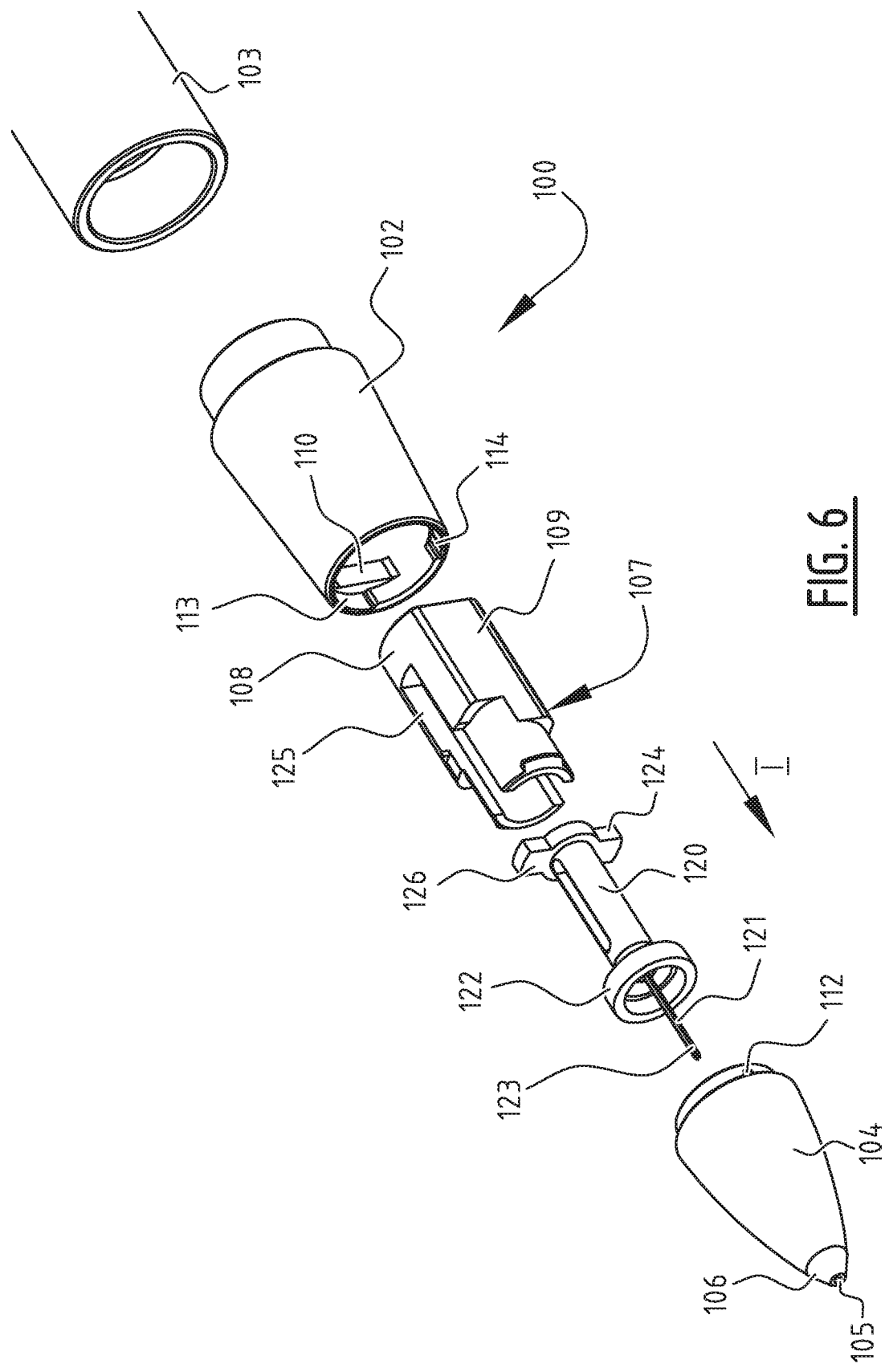
FIG. 6 shows the embodiment of FIG. 5, wherein the needle module and spacer are shown in an exploded view.

The same embodiment of the device 100 is shown in FIG. 6, wherein the needle module 101 and spacer 102 are shown in an exploded view. In an assembled state of needle module 101, the distal housing part 104 and main housing part 107 contain the needle unit 120, which comprises one or more needles 121, and an elastic element 122. The needle unit 120 is movable with respect to the housing of the needle module. The elastic element is arranged as biasing means for holding the needle distal end 123, that is the tip section of the needle including the sharp point, within the housing in case no force is applied on the needle unit 120 in direction I for pushing the needle distal end 123 through the opening 105. The needle unit 120 further comprises an outwardly extending protrusion 124, which are arranged to be placed in the corresponding groove 125 of the main housing part 107. The needle unit 120 is thus movable with respect to the housing in direction I, which is the longitudinal direction of the device 100.

FIG. 7a shows a cross-section of a snapshot of the mounting procedure at a time that the needle module 101, and more specifically the main housing part 107, is inserted in the spacer 102. The spacer 102 is in turn connected to the driving device 103, which comprises a driving rod 130 for driving the proximal end 127 of the needle unit 120. A reservoir 128 for coloring agent is provided near the tip 106 of the distal housing part 104.

In FIG. 7b the device 100 is shown again, wherein the needle module 101 is in a coupled state with the spacer 102. During the mounting process, the driving rod 130 will come in contact with the proximal end 127 of the needle unit 120, when the needle module 101 is pushed further on the spacer 102, the needle unit 120 is forced to move within the housing in the longitudinal direction towards the tip 106 of the distal housing part 104 towards the intermediate position. Thereby the elastic element 122 is deformed, such that an elastic force in the direction of the driving device 103 is generated. The proximal end 127 of the needle unit 120 is, due to this pre-stress effect, thus urged to keep contact with the distal end 131 of the driving rod 130. During this process the needle distal end 123 will puncture and penetrate the reservoir 128, after which the coloring agent, for instance ink, is allowed to flow over the needle 121. The device 100 is now ready to be driven in a reciprocal manner.

When driving the device 100, the needle 121 reciprocally moves from the position as shown in FIG. 7b to the position shown in FIGS. 8a and 8b, where the needle distal end 123 is in the extended position. The cross section shown in FIG. 8b is rotated 90 degrees around the longitudinal axis 140 of the device 100, thereby also showing that the spacer 102 and needle module 101 are not fully axisymmetric. In the extended position, the needle distal end 123 extends a certain maximum distance d3 from the hole 105, arranged in the tip 106 of the distal housing part 104. Thereby, the needle 121 can only penetrate the skin with a depth equal or less to the maximum distance d3. Thus, coloring agent that is allowed to flow along the needle 121 from the reservoir 128 is inserted into the skin at a depth equal or less to the maximum distance d3. Due to this, the depth for inserting coloring agent can be regulated and one can ensure that the ink is only deposited in the top layers of the skin, thereby creating temporary marks in the skin.

Note that after mounting of the needle module 101 in the previously prescribed manner, the displacement of the needle unit 120, and thus the needle distal end 123, will be limited, as a frontal side 126 of the outwardly extending protrusion 124 will abut an inner side of the inner retaining wall 110 of the spacer 102 if a large enough force, for overcoming the elastic forces of the elastic element 122, is applied on the needle unit 120 in direction I for pushing the needle distal end 123 through the opening 105. Hence, the maximum distance d3 the needle 121 is allowed to extend from the distal end 104 of the housing is thereby determined by the cooperation between front surface 126 of the outwardly extending protrusion 124 and a surface of the inner retaining wall 110, as is clearly seen in FIG. 8b. In general, by arranging the limiting mechanism as cooperating stop surfaces on the needle module 101 and spacer 102, the maximum distance d3 can easily be determined, from a limited number of dimensional parameters of the device 100:

$$d3 = d6 - d5 - d4$$

wherein d6 represents the distance from the front surface 126 of the outwardly extending protrusion 124 to the needle distal end 123, thereby representing the effective length of the needle unit 120, d5 is the length of the distal housing part 104 and d4 is the width (or thickness) of the inner retaining wall 110. As in a standardized needle module 101, lengths d6 and d5 are given, the maximum distance d3, representing the maximum skin penetration depth, can easily and reliable be varied by changing the dimensions of the inner retaining wall 110 of the spacer.

The elastic element 122 of the device 100 is made from a sheet of rubber like material to act as a tension spring, as was shown more clearly in FIGS. 7a-8b. Obviously, other types of elastic elements can also be applied, for instance compression springs made from suitable elastic materials such as, for instance, steel, as is also shown in FIGS. 2, 3 and 9a-9c.

Figure 9B:
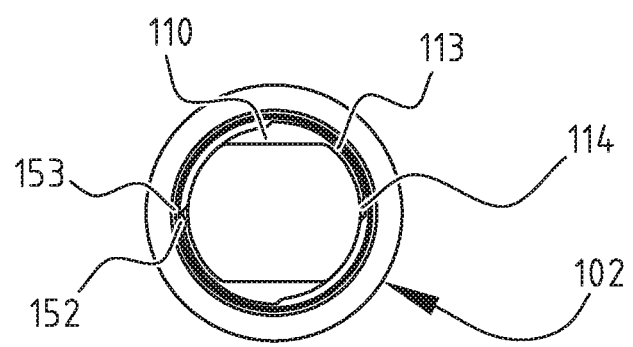
Figure 9C:
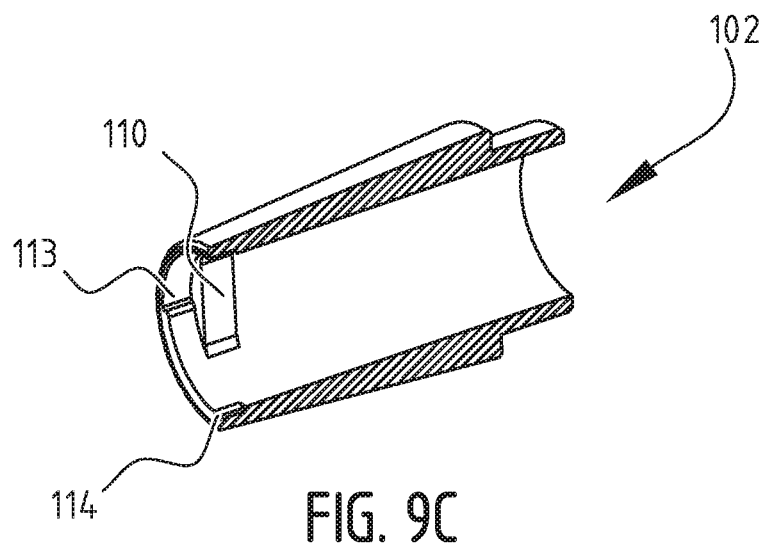

The spacer is shown in more detail in FIGS. 9a-9c. Even tough the side 150 for connecting the spacer 102 to the driving device 103, it can be connected using any suitable connecting means, for instance a similar bayonet connection. Near the distal end 151 of the spacer 102, the connecting features are shown in more detail. In this embodiment, the spacer 102 is provided with inner retaining walls on both sides of the spacer 102. In addition, the recesses 113 for receiving the corresponding small protrusions 112 provided on the distal housing part 104 can clearly be seen. At the first end 114 of the recesses 113, it is seen that the recess is provided with a small upstanding feature 152, followed by a cavity 153 arranged adjacent to the upstanding feature 152. As the needle module 101 is inserted into the spacer 102, the small protrusion 112 provided on the distal housing part 104 are received by the recess 113. The needle module 101 is then rotated around its axis, where after the small protrusion 112 contact the upstanding feature 152. By applying sufficient torque, the spacer 102 and/or distal housing part 104 will slightly deform, allowing the small protrusion 112 to pass upstanding feature 152 and snap into the cavity 153 arranged for receiving the small protrusion 152.

FIGS. 10a-10c show more schematically an alternative embodiment of the device 200. The device 200 comprises a needle module 201, spacer 202 and driving device 203, which are interconnected by means of a bayonet connection, as was described in detail in the previous embodiment, a snap-fit connection, screw connection or any other suitable connection. The needle module 201 comprises a housing 204, which can comprise of multiple housing parts, a needle unit 220, which is substantially enclosed by the housing in its retracted state and comprises at least a needle 221. The needle unit 220 is movable with respect to the housing 204 in the direction I, direction I being parallel to the longitudinal axis 240 of the device 200. Biasing means, being an elastic element 222, such as a spring or any other suitable element, as provided for urging the needle unit 220 to the retracted or intermediate position, wherein the needle distal end 223 is maintained within the housing 204. An outwardly extending protrusion 224, which is a part of the limiting mechanism as is explained later, is again provided near the proximal end 227 of the needle unit 220.

The spacer 202 is again arranged to be connected to the needle unit 201 at its distal end 251 and to the driving device 203 at its proximal end 252. A blocking surface on the proximal end of the inner retaining wall 210, which is arranged on the inner circumferential wall of the spacer, cooperates with a matching blocking surface arranged on a housing coupling protrusion 219 of the needle module 201 for coupling the needle module 201 to the spacer 202.

The driving device 203 depicted in the embodiment, comprises a decoupling mechanism 260 for at least partly decoupling the motion of the driving rod 230 for driving the proximal end 227 of the needle unit 220 and the motor 261 for generating the reciprocal motion. The motor 261 is fitted with a transfer module 262, comprising a swash-plate 271 or any other suitable mechanism that transfers a rotational motion into a reciprocal translational motion, for converting the output of the motor 261 to a suitable reciprocal motion for driving the needle unit 220. The decoupling mechanism 260 further comprises a sliding member 263, which is movable in direction 1 with respect to the driving rod 230 and a guiding member 264 being fixed to the housing 265 of the driving device 203.

A first coupling spring 266, or any other suitable biasing means, urges the driving rod 230 and sliding member 263 in opposite directions with respect to each other. For this purpose, the first coupling spring 266 is provided between a driving rod attachment point 268 and a sliding member attachment point 270. The first coupling spring 266 is preferably pre-stressed by imposing an initial deformation. In order to ensure that the coupling mechanism 260 in maintained, the driving rod is provided with securing means, such as an abutment shoulder 269, which locks behind the sliding member attachment point 270 and ensures the integrity of the decoupling mechanism 260.

A second coupling spring 267, or any other suitable biasing means, is provided between the driving rod attachment point 268 and a guiding member distal end 272 for urging the driving rod 230 in the direction of the motor 261. Hence, the second coupling spring 267 pushed, through the driving rod 230, the first coupling spring 266 and the sliding member 263, a sliding member contact end 273 against the swashplate 271. Thereby, it is ensured that the sliding member 263 follows the motion of the swashplate 271, as can also be verified in FIGS. 10b and 10c. This results in the desired reciprocal motion of the sliding member 263, which is fed through the decoupling mechanism 260 to the movable needle unit 220.

In FIGS. 10b and 10c, the needle 221 has reached the maximum extending distance d3, at which point the outwardly extending protrusion 224, which is a part of the limiting mechanism, contacts the inner retaining wall 210 of the spacer, as is shown in more detail in FIG. 11. Thus the means for limiting the maximum extending distance d3 (i.e. the limiting mechanism) are formed by the mutual cooperation between the spacer 202 and the housing 204 of the needle module 201. In the embodiment shown, the inner retaining wall 210 is a stepped protrusion, comprising a first step 281 and a second step 282. The a surface of the outwardly extending protrusion 224 abuts a surface of the first step 281 of the inner retaining well 210, thereby blocking the needle unit in the direction I towards the opening 205 located at the distal end of the device 100. The needle unit 201 is connected through the spacer 202 by locking the housing coupling protrusion 219 with the second step 282 of the inner retaining wall 210. It should be noted that, in this coupled state, the outwardly extending protrusion 224 will not be able to abut the second step 282 or the housing coupling protrusion 219.

The working principle of the decoupling mechanism is further clarified by means of FIGS. 10b and 10c. In FIG. 10a, the needle is in the intermediate position, such that the needle distal end 223 extends in the housing. In FIGS. 10b and 10c show the needle distal end 223 in its maximum extended position d3, the difference is however that in FIG. 10b the drive, in this case the swashplate 271, has not reached its maximum displacement yet. In FIG. 10b it is seen that the abutment shoulder 269 of the driving rod 230 is still kept in contact with the sliding member attachment point 270 by the, preferably pre-tensioned, first coupling spring 266. At this point, the needle unit 220 is blocked by the limiting means, as explained before, the driving rod 230, whose distal end 231 is in direct contact with the proximal end 227 of the needle unit 220, is thereby also blocked from moving further towards the distal end of the device in the direction I. Hence, a relative displacement between the driving rod 230 and the sliding member 263 occurs as the swashplate 271 moves towards its maximum displacement, thereby also pushing the sliding member 263 to its maximum displacement. Due to this relative displacement, the first coupling spring 266 deforms, thereby applying a reaction force on the sliding member 263 to urge the sliding member towards the proximal end 241 of the device and a reaction force on the driving rod 230 to urge the driving rod 230 towards the needle unit 220. As the swashplate 271 moves from its maximum displacement, the first coupling spring 266 is allowed to expand again, thereby urging the sliding member 263 to follow the movement of the swashplate 271, as the sliding member contact end 273 is forced to keep contact with the swashplate 271. At a certain point in the return movement of the sliding member 263, the abutment shoulder 269 will contact the sliding member attachment point again, thereby the driving rod 230 and the sliding member 263 will move as one, whereafter the needle unit 220 is urged towards the retracted position by the elastic element 220. Hence, the needle distal end 223 jointly moves with the needle unite 220 whereby it retracts into the housing 204 again. As the motor 261 is arranged to be driven continuously for longer or shorter time instances, a reciprocal motion of the needle distal end 223 is obtained.

Clearly, the decoupling mechanism 260 ensures that the maximum extending distance d3 of the needle distal end 223 can accurately be set and maintained. Without this decoupling mechanism 260, the excess stroke of the driving device 203 would have to be taken up in the elastic or plastic deformation of the different parts of the device 200, potentially leading to excessive forces applied on, and damage to, the different parts of the system, compromising its functionality and accuracy.

Note that all the different embodiments of the needle unit 1, 101, 201, the spacer 3, 102, 202 and the driving device 103, 203 can be combined. In addition, the present invention is not limited to the embodiment shown, but extends also to other embodiments falling within the scope of the appended claims.

The invention claimed is:

1. A needle module for use in a device for puncturing skin in a reciprocal manner, the device comprising:
  a needle module that comprises a needle unit, a housing, and a biasing mechanism, wherein the needle module is configured to be removably connected to a driving device, the driving device being configured for reciprocally moving the needle unit by means of a driving rod which is driven by a motor, wherein:
  the needle unit comprises a needle;
  the needle unit is movable with respect to the housing between an extended position, in which a distal end of the needle extends from a distal end of the housing, and a retracted position, in which the distal end of the needle is positioned within the housing;
  the biasing mechanism is arranged for urging the needle unit towards the retracted position;
  the device further comprises a limiting mechanism arranged for limiting a relative movement of the needle unit out of the distal end of the housing to a maximum extension distance of 1.5 mm or less when the needle unit is moving towards the extended position, and
  wherein the biasing mechanism and/or the limiting mechanism is arranged for limiting, in the retracted position, a displacement of a proximal end of the needle in the housing such that the proximal end of the needle is retained in the housing.

2. The needle module according to claim 1, wherein the limiting mechanism comprises mutually cooperating stop surfaces for limiting the relative movement of the needle unit and the housing.

3. The needle module according to claim 2, wherein an interior of the device is arranged with protrusions and/or recesses for cooperating with protrusions arranged on an exterior of the needle unit.

4. The needle module according to claim 2, whereby at least one of the mutually cooperating stop surfaces is substantially ring-shaped.

5. The needle module according to claim 1, wherein:
  the limiting mechanism is at least partially formed by the biasing mechanism; and the biasing mechanism is arranged for limiting the relative movement of the needle unit out of the distal end of the housing to the maximum extension distance.

6. The needle module according to claim 1, wherein:
the housing of the needle module comprises a main housing part and a removable distal housing part; and
the limiting mechanism is at least partially arranged in the main housing part.

7. The needle module according to claim 2, wherein the housing comprises one of the stop surfaces at or near the distal end of the housing.

8. The needle module according to claim 1, wherein the biasing mechanism engages the needle unit at a first location and wherein the needle unit is provided with a stop surface at a location at a distance from the first location.

9. The needle module according to claim 1, wherein, in the retracted position, a proximal end of the needle is in the housing.

10. The needle module according to claim 9, wherein the limiting mechanism is further arranged for limiting, in the retracted position, a displacement of the proximal end of the needle, such that the proximal end of the needle is retained in the housing.

11. The needle module according to claim 9, wherein the biasing mechanism is further arranged for retaining the proximal end of the needle in the housing.

12. The needle module according to claim 1, wherein the housing comprises a reservoir containing a coloring agent for introduction in the skin.

13. The needle module according to claim 12, wherein:
the reservoir is arranged at or near the distal end of the housing; or
the coloring agent is ink.

14. The needle module according to claim 12, wherein the reservoir contains less than 0.3 ml of the coloring agent.

15. The needle module according to claim 12, wherein the distal end of the needle is reciprocally movable in and out of the reservoir when the needle unit is moving between the retracted and extended position.

16. The needle module according to claim 12, wherein, in the retracted position, the distal end of the needle extends at a proximal distance from the reservoir.

17. The needle module according to claim 16, wherein, upon coupling the needle module to the driving device, the needle unit is movable to an intermediate position that is located between the extended and retracted position and in which the needle unit extends within the reservoir.

18. The needle module according to claim 17, wherein the distal end of the needle extends in the reservoir in the intermediate position.

19. The needle module according to claim 12, wherein:
the housing comprises:
a first film arranged near the distal end of the housing; and
a second film arranged further from the distal end of the housing; and
the reservoir is positioned between the first film and the second film.

20. The needle module according to claim 12, wherein:
the reservoir comprises a cartridge for holding the coloring agent;
the cartridge can be punctured by the needle; and
the housing is arranged for holding the cartridge.

* * * * *